United States Patent
Wen et al.

(10) Patent No.: US 9,457,034 B2
(45) Date of Patent: Oct. 4, 2016

(54) MAGNETIC MICROSPHERE AND METHOD OF FORMING A MICROSPHERE

(75) Inventors: Weijia Wen, Kowloon (HK); Ping Sheng, Sai Wan Ho (HK); Xiuqing Gong, Kowloon (HK); Suili Peng, Kowloon (HK)

(73) Assignee: THE HONG KONG UNIVERSITY OF SCIENCE AND TECHNOLOGY, Kowloon (HK)

( * ) Notice: Subject to any disclaimer, the term of this patent is extended or adjusted under 35 U.S.C. 154(b) by 1004 days.

(21) Appl. No.: 12/619,196

(22) Filed: Nov. 16, 2009

(65) Prior Publication Data

US 2010/0124572 A1    May 20, 2010

Related U.S. Application Data

(60) Provisional application No. 61/199,251, filed on Nov. 17, 2008.

(51) Int. Cl.

| | |
|---|---|
| *A61K 9/66* | (2006.01) |
| *A61K 9/50* | (2006.01) |
| *A61K 31/616* | (2006.01) |
| *A61K 31/43* | (2006.01) |
| *A61K 31/60* | (2006.01) |
| *A61K 9/00* | (2006.01) |
| *A61K 9/51* | (2006.01) |

(52) U.S. Cl.
CPC ............ *A61K 31/60* (2013.01); *A61K 9/0009* (2013.01); *A61K 9/5031* (2013.01); *A61K 9/5036* (2013.01); *A61K 9/5138* (2013.01); *A61K 31/43* (2013.01); *A61K 31/616* (2013.01)

(58) Field of Classification Search
None
See application file for complete search history.

(56) References Cited

U.S. PATENT DOCUMENTS

| | | | |
|---|---|---|---|
| 5,411,730 A | 5/1995 | Kirpotin et al. | |
| 6,413,548 B1 * | 7/2002 | Hamer et al. | 424/489 |
| 6,479,146 B1 | 11/2002 | Caruso et al. | |
| 6,616,946 B1 * | 9/2003 | Meier et al. | 424/489 |
| 2004/0210289 A1 * | 10/2004 | Wang et al. | 607/116 |
| 2006/0041182 A1 | 2/2006 | Forbes et al. | |
| 2007/0092914 A1 | 4/2007 | Griffiths et al. | |
| 2008/0074449 A1 | 3/2008 | Lee et al. | |

OTHER PUBLICATIONS

Gong, Xiuqing, et al., "Design and Fabrication of Magnetically Functionalized Core/Shell Microspheres for Smart Drug Delivery", 2009, pp. 292-297, Issue 19, Advanced Functional Materials.
Peng, Suili, et al., "Magnetically responsive elastic microspheres", 2008, vol. 92, 012108, Applied Physics Letters.
Papisov, M.I., et al., "Possible use of ferromagnetic materials for targeted drug transport", 1984, pp. 1289-1291, Plenum Publishing Corporation.
Anna, Shelley L., et al., "Formation of dispersions using "flow focusing" in microchannels", 2003, pp. 364-366, vol. 82, No. 3, Applied Physics Letters.
Seo, Minseok, et al., "Microfluidic consecutive flow-focusing droplet generators", 2007, pp. 986-992, vol. 3, Soft Matter.
Xia, Younan, et al., "Soft Lithography", 1998, pp. 153-184, vol. 28, Annual Review of Materials Science.
Massart, René, "Preparation of Aqueous Magnetic Liquids in Alkaline and Acidic Media", 1981, pp. 1247-1248, vol. MAG-17, No. 2, IEEE Transactions on Magnetics.

* cited by examiner

*Primary Examiner* — Abigail Fisher
*Assistant Examiner* — Frank Choi
(74) *Attorney, Agent, or Firm* — Nath, Goldberg & Meyer; Jerald L. Meyer; Stanley N. Protigal

(57) ABSTRACT

The microspheres have many possible applications including smart drug delivery, breaking and damper devices. In one arrangement, a microsphere comprises a shell 120 and a core 110. The core comprises a liquid, which may be a drug, while the shell comprises magnetic particles. The microsphere is deformable in response to application of an external magnetic field. Also disclose is an arrangement in which a microsphere has a magnetic core and a PDMS shell.

6 Claims, 10 Drawing Sheets

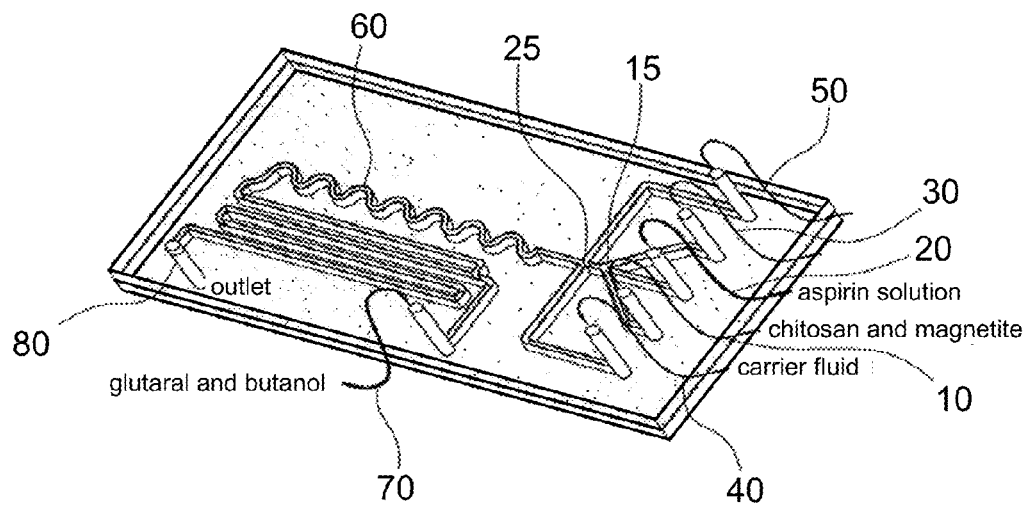
Fig. 5A
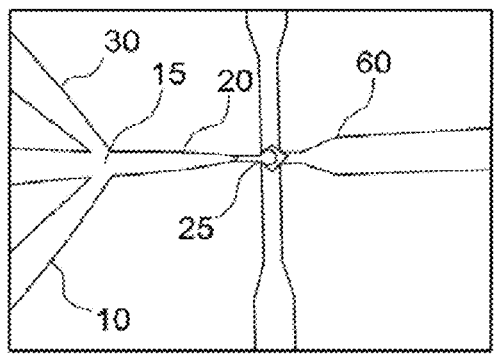 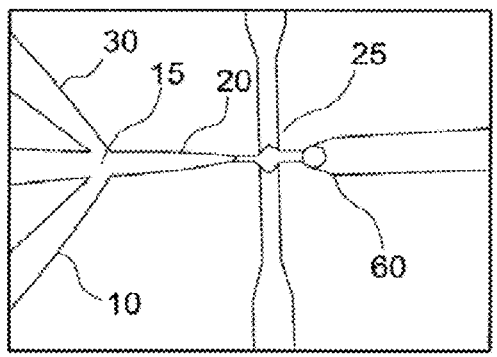
Fig. 5B  Fig. 5C
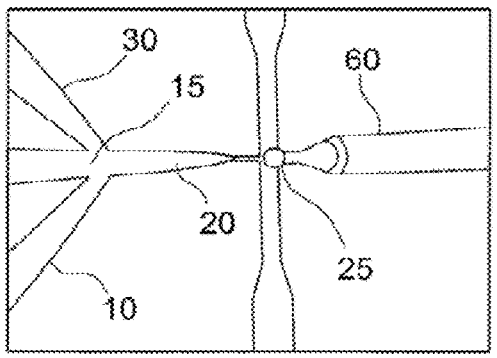 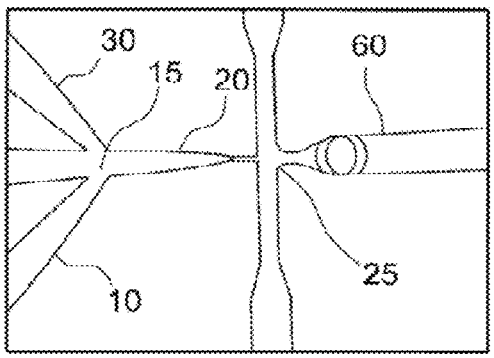
Fig. 5D  Fig. 5E

MAGNETIC MICROSPHERE AND METHOD OF FORMING A MICROSPHERE

CROSS REFERENCE TO RELATED APPLICATIONS

This application claims benefit of U.S. Provisional Application No. 61/199,251 filed Nov. 17, 2008 (which is hereby incorporated by reference).

FIELD

The disclosure relates to magnetic microspheres and methods of forming the microspheres. The microspheres have many possible applications including, but not limited to, smart drug delivery, braking and damping devices, a controllable elastomer ball array and a single spherical micro-damper. The disclosure also relates to a method of dispensing a liquid, especially but not necessarily a drug, using the microspheres.

BACKGROUND

In the field of medicine, it is known to encapsulate a drug inside a microsphere in order to provide a method of delivery to a patient, e.g. by ingestion. In a separate development, in recent years, attention has been given to use of magnetic drug carriers for the purpose of guiding the drug to a specific location by a magnetic field, or for use in magnetic resonance imaging.

SUMMARY

It would be desirable to control the time at which a liquid, especially a drug, is released from a microsphere and/or to provide a mechanism for triggering the release of the liquid. Furthermore it would be desirable to control the rate at which a liquid is released. While the disclosed technology may find application to many liquids, it will be especially useful where the liquid is a drug.

A first aspect of the disclosed technology provides a microsphere comprising a shell and a core. The core comprises a liquid while the shell comprises magnetic particles. The microsphere is deformable in response to a magnetic field and may be caused to expand and/or contract by application of a magnetic field. Deformation of the microsphere causes some or all of the liquid in the core to be dispensed.

Preferably the core comprises a drug in liquid form. In this way the time at which the liquid (e.g. the drug) is released may be controlled. For example, release of the drug may be initiated or accelerated by application of a magnetic field to deform the microsphere. Furthermore, the rate at which the drug is released may be controlled by varying the strength, or other characteristics, of the magnetic field.

The magnetic field may be varied, for example in the form of a periodic waveform. This causes the microsphere to expand and contract sequentially, which has a pumping effect on the liquid in the core causing it to be released from the microsphere.

Preferably the microsphere is elastically deformable. The shell may comprise a plurality of magnetic particles in an elastically deformable substrate. The microsphere preferably comprises magnetic particles in a matrix of organic material. The organic material may for example, be an elastomer, a silicon oil, or any suitable polymer. Preferably the shell is cross-linked.

The drug is preferably water soluble. The drug may, for example, comprise aspirin or amoxicillin. The magnetic particles may comprise magnetite. In one embodiment the shell comprises magnetite particles, an aqueous solution of acetic acid and chitosan.

Preferably the microsphere has a diameter of 50 to 200 microns. The diameter refers to the diameter of the microsphere in the 'undeformed' substantially spherical rest state.

A second aspect of the disclosed technology provides a method of forming a microsphere comprising the steps of providing a first fluid, providing a second fluid comprising magnetic particles and mixing said first and second fluids such that the first fluid forms a core of the microsphere and the second fluid forms a shell of the microsphere. Preferably the first fluid comprises a drug.

Preferably the shell formed by the second fluid is elastically deformable. In a preferred arrangement the first and second fluids are mixed using a fluid flow device comprising a plurality of channels. Preferably the device has at least first, second and third channels, with the second channel being provided between the first and third channels. The first and third channels join with the second channel at a first junction. The first fluid is injected into the second channel and the second fluid is injected into the first and third channels. The junction has a flow focusing function that causes the first fluid in the second channel to form a core which is enveloped by the second fluid from the first and third channels. Each channel has a flow rate and the flow rates of the channels are adjusted so as to form a co-axial jet with the first fluid forming a core enveloped by a shell of the second fluid.

The fluid flow device may have fourth and fifth channels outward of the first to third channels. The fourth and fifth channels join said second channel at a second junction which is downstream of said first junction. A carrier fluid is injected into the fourth and fifth channels. The carrier fluid may be an oil, for example sunflower oil. It enables the microspheres formed by the first and second fluid to pass through the channel downstream of the second junction, without adhering to the sides of the channel.

The method preferably further comprises a process for solidifying the shell formed by the second fluid. The solidifying process may comprise one or more of the following: photo-polymerization, heating, hydrolysis, condensation, de-wetting coacervation or another chemical reaction. Here "dewetting" means drawing the solvent out of a droplet's outer layer. The solidifying process may comprise adding a de-wetting agent (e.g. to draw out water) from the shell of the microsphere. The de-wetting agent may be injected into the channel downstream of the first or second junction. Suitable de-wetting agents include, but are not limited to, butanol, ethanol and propanol. The solidifying process may comprise a cross-linking reaction. For example, a cross linking re-agent may be injected into the fluid flow device, preferably downstream of the first or second junction. In one embodiment glutaraldehyde was used as cross linking re-agent, however other alternative re-agents will be apparent to a person skilled in the art. The solidifying process may comprise heating the microsphere, for example by heating the fluid flow device or a channel within the fluid flow device. The solidifying process may involve quenching in order to absorb excess de-wetting agent. For example, a quenching agent may be injected into a channel of the fluid flow device. In one embodiment, the quenching agent comprised oleic acid.

A third aspect of the disclosed technology provides a method of dispensing a liquid comprising providing a microsphere having a liquid core and a shell comprising magnetic particles and applying a magnetic field across the microsphere in order to deform the microsphere.

Preferably the magnetic field is varied and the microsphere expands and contracts as the magnetic field is varied. This has a pumping effect on the liquid causing at least a portion of the liquid to be expelled from the microsphere. The magnetic field may be varied periodically in a regular fashion (i.e. a periodic waveform). The magnetic field may be an alternating magnetic field and may be provided by an electromagnet.

When the sphere is deformed, e.g. into an ellipsoidal shape, liquid from the core is leaves the microsphere through the shell. The shell is preferably permeable to the liquid in the core, at least when it is stretched. The stretching may increase the degree of permeability. Preferably the shell is elastically deformable.

The core liquid preferably comprises a drug. In this way the method may be used to control delivery of a drug. In particular the time of release and the rate of release may be controlled by application of the magnetic field. The rate of release is influenced by the strength of the magnetic field, the frequency of the magnetic field and the type of waveform. A stronger magnetic field and a higher frequency both lead to an increased rate of release. The magnetic field may for example be varied in a step wave form, sinusoidal wave, or a saw wave. The more rapid the increase or decrease of the magnetic field the more rapidly the drug is released. Thus the step wave form causes a higher rate of release than the sinusoidal waveform.

A fourth aspect of the disclosed technology provides an apparatus including one or more microspheres according to the first aspect of the disclosed technology and a device for generating a magnetic field and varying said magnetic field. The device may, for example, be an electromagnet. The device has a controller for varying the strength of the magnetic field and a controller for varying the frequency of the magnetic field.

The apparatus can be used to control the release of a liquid, especially a drug, from the core of the microsphere.

A fifth aspect of the disclosed technology provides a microsphere comprising magnetic particles surrounded by elastically deformable material; the microsphere being elastically deformable in response to application of an external magnetic field. Preferably the modulus of elasticity of the elastically deformable material is at least 120 kPa ($1.2 \times 10^5$ N/m$^2$), more preferably at least 200 kPa. In some arrangements the modulus of elasticity may be in the range 200-1000 kPa, or 350 to 800 kPa. Preferably the stiffness of the microsphere may also be varied in response to application of a magnetic field.

The ability of the microsphere to change its shape and/or stiffness in response to a magnetic field is very useful and has many applications. For example the microsphere may be used in braking and damping devices, a controllable elastomer ball array or as a spherical micro-damper.

The microsphere preferably comprises an elastically deformable organic material and magnetic particles.

Preferably the organic material is a hydrocarbon oil; most preferably a silicon oil. The silicon oil may be PDMS. Alternatively the organic material may be a rubber based material. The magnetic particles are preferably nano or microsized.

In one arrangement the microsphere comprises a magnetic core surrounded by an organic material shell. The magnetic core may be a magnetic colloid. In this case the organic material shell is elastically deformable. When a magnetic field is applied the magnetic core may expand or contract in response to the magnetic field and the shell deforms to accommodate this expansion or contraction.

In an alternative arrangement the microsphere is a single phase structure comprising a plurality of magnetic particles dispersed in an organic substrate. The magnetic particles are preferably magnetite. The magnetic particles may be nano or micro sized. 'Single phase structure' means a one phase structure, rather than a core shell structure. Typically the one phase structure will be a organic material (e.g. a gel) in which a plurality of magnetic particles are dispersed. The one phase microsphere may comprise silicone oil, PDMS gel and magnetic particles, the magnetic particles being 20% by weight.

A sixth aspect of the disclosed technology provides a microsphere comprising magnetic particles in an elastically deformable matrix; the stiffness of the microsphere being variable in response to application of a magnetic field.

A seventh aspect of the disclosed technology provides a method of making the microsphere of the fifth or sixth aspect of the disclosed technology comprising the step of providing a fluid flow device having at least first, second and third channels, said second channel being provided between said first and third channels, said first and third channels joining with said second channel at a first junction; injecting a first fluid is comprising magnetic material into the second channel and injecting a second fluid into the first and third channels; mixing the fluids at the junction such that the first fluid forms a core and the second fluid forms a shell of the microsphere. This method makes a core-shell microsphere.

An eighth aspect of the disclosed technology provides a method of making the microsphere of the fifth or sixth aspect of the disclosed technology comprising the step of forming droplets of a fluid in a fluid flow device, the fluid comprising an organic material and magnetic particles.

Preferably the fluid flow device comprises first and second channels which join together to form a third channel, the junction having a flow focusing effect. The fluid may comprise PDMS gel, silicone oil and magnetic particles at a concentration of 20% by weight. This method makes a single phase microsphere.

Features of any of the fifth to eighth aspects of the disclosed technology may be combined together.

BRIEF DESCRIPTION OF THE DRAWINGS

Examples of the disclosed technology will now be described, by way of example only, with reference to the accompanying drawings in which:—

FIGS. 2A to 2E show the reaction of the microspheres to a magnetic field;

FIG. 5A shows a fluid flow device for forming a magnetic microsphere;

FIGS. 5B to 5E are diagrams showing steps in the process of forming the microsphere;

DETAILED DESCRIPTION OF PREFERRED EMBODIMENTS

Figure 1:
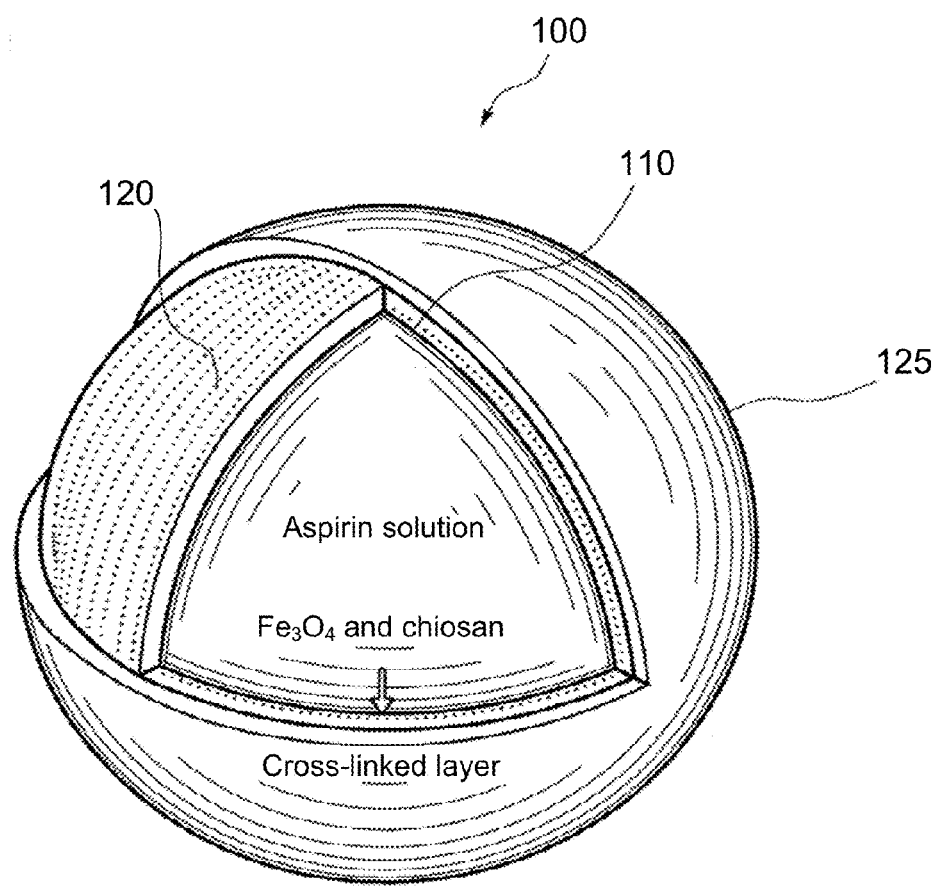
FIG. 1 shows a microsphere comprising a liquid drug core and a shell with magnetic particles.

FIG. 1 shows a microsphere comprising a core 110 and a shell 120. The core comprises a drug in liquid form, for example aspirin in an aqueous solution. The core comprises magnetic particles in an organic material substrate or matrix. In a preferred embodiment the shell comprises magnetite particles in a chitosan substrate. The shell 120 is preferably cross-linked, e.g. the chitosan may be cross-linked to form a solid skin for the microsphere.

The microsphere is deformable by application of an external magnetic field. FIG. 2A shows the microsphere when the magnetic field is zero. It has a diameter of d. FIG. 2B shows the microsphere when the magnetic field is increased and the microsphere is stretched along the direction of the field into an ellipsoidal shape. This is due to the magnetic particles forming chains aligned along the field direction, due to the dipole-dipole interaction between the particles. When stretched the microsphere has a diameter of $d+\Delta d$ along its longest axis. When the magnetic field strength reached 3000 G, the observed deformation d/d of a core-shell microsphere was 6.3%.

The external field also tends to align randomly dispersed microspheres into a line along the direction of the field. This is shown in FIGS. 2C to 2E.

Figure 2F:
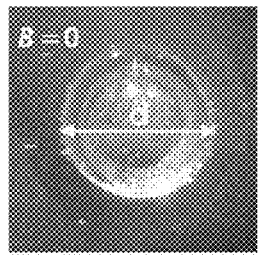
FIG. 2F shows deformation of the microspheres with increasing magnetic field.
Figure 2F:
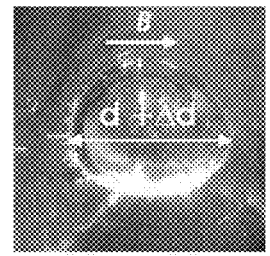
Figure 2F:
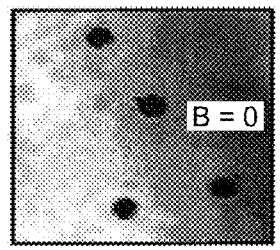
Figure 2F:
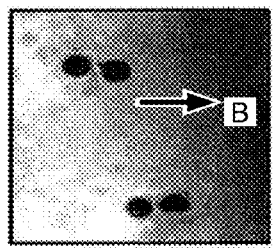
Figure 2F:
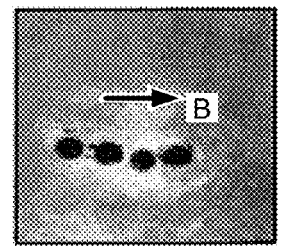
Figure 2F:
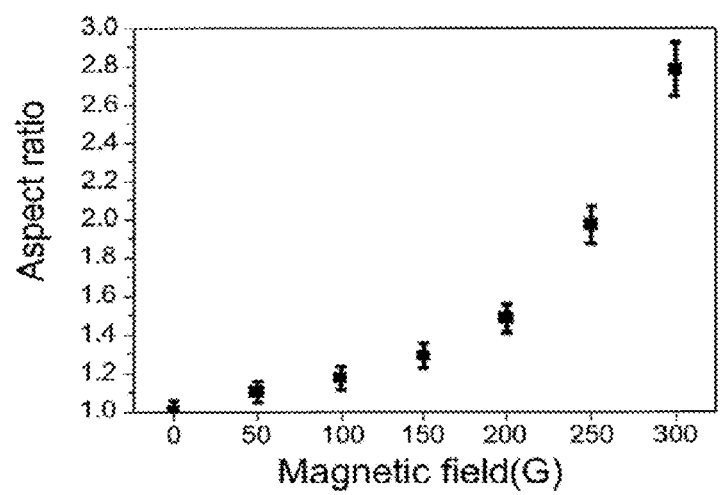

This stretching phenomena also occurred when the magnetic field was periodically varied as an alternating magnetic field (e.g. a field produced by an AC electromagnet). FIG. 2F shows the elongation of the microspheres under 100 G, 200 G and 300 G magnetic fields when frequency of the field was 5 Hz. The x axis of the graph represents the magnetic field strength, while the y axis of the graph represents the aspect ratio $(d+\Delta d)/d$. As can be seen from the graph, the degree of extension could be adjusted by varying the strength of the magnetic field. It was observed that when the microspheres changed their shapes from spherical to ellipsoidal, the drug solution was released through the cross-linked shell. This effect is discussed in more detail below.

To study the effect of magnetically responsive behavior on drug release rate, we measured the aspirin release under magnetic field. Aspirin-release characteristics were determined by UV/VIS spectra carried out with Perkin Elmer Lambda 20 UV/VIS spectroscopy, where the aspirin concentration indication line was chosen at the maximum absorption wavelength of 296 nm. For each measurement, microspheres (2 g) were stored in a dialysis bag (4.times.4 cm). The aspirin release efficiency was accessed in 3 ml PBS. In order to study the aspirin release activated under an applied magnetic field, an electromagnet with two parallel poles (PHEWY Products, Germany) was used to generate a homogeneous magnetic field, in which the dialysis bag was placed. A PM 5139 function generator (PHILIPS) and stereo power amplifier 216 (THX, LUCASFILM Co.) were used to create pulsed signals. Absorbance measurement was performed on a ND-1000 spectrophotometer at $\lambda_{ex}=495$ nm (DIAMed).

Magnetic fields with different strength, frequency and time variation profile were applied to the sample. We used a dialysis technique to measure the release and the percentage of cumulatively released aspirin C was defined as $$C = \frac{C_i}{C_a} \times 100 \qquad (1)$$

Here Ci is a cumulative amount of released aspirin for each measurement, while Ca is the total amount of aspirin—the encapsulated amount. We defined the total amount of aspirin as that in a 1 ml syringe which is 10 mg, since for each measurement a 1 ml syringe of aspirin solution was used to make one dialysis bag. Each measurement was repeated three times and the average value was calculated.

Figure 3A:
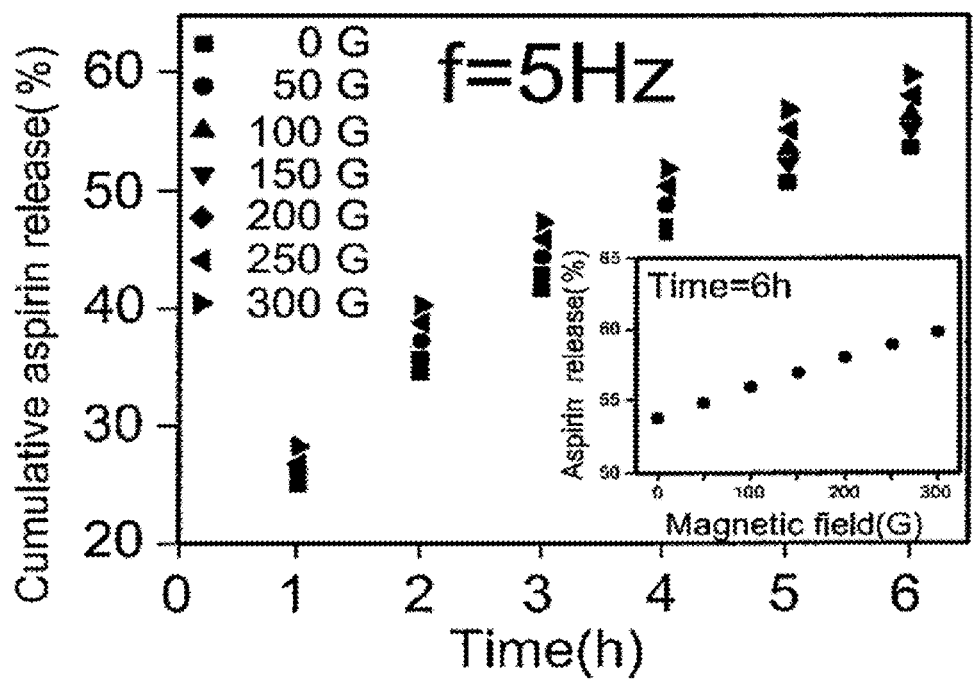
FIG. 3A shows drug release over time for different strengths of magnetic field.

FIG. 3A is a graph showing the cumulative release of aspirin over time for microspheres to which magnetic fields of between 0 and 300 G were applied. The frequency of the magnetic field was fixed at 5 Hz. It can be seen that the applied magnetic field enhanced the rate of release. Increasing the strength of the magnetic field increased the rate of release.

Figure 3B:
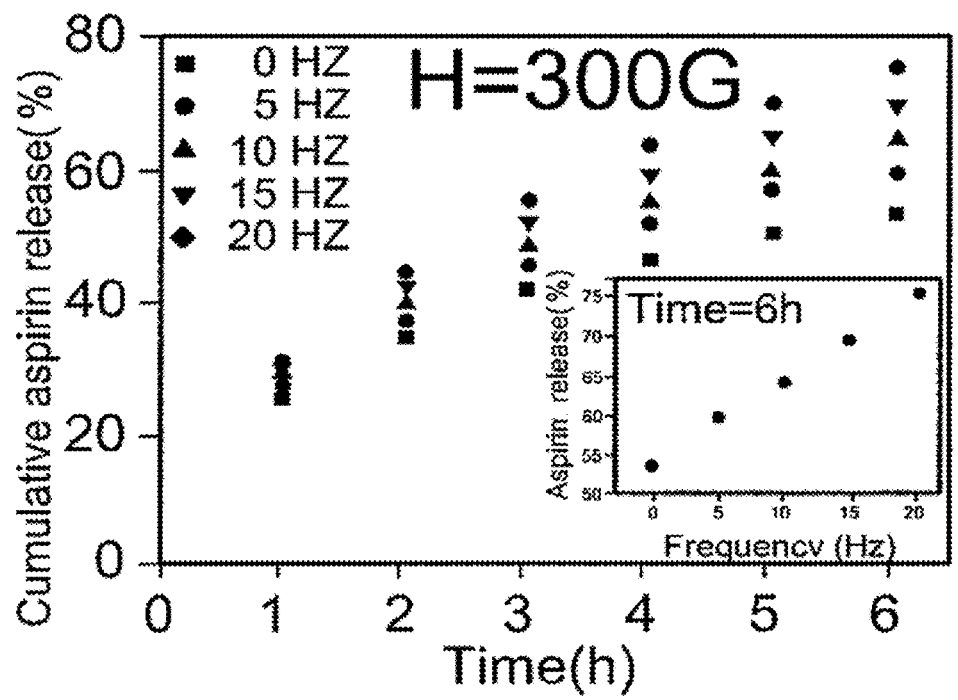
FIG. 3B shows drug release over time for different frequencies of magnetic field.

FIG. 3B is a graph showing the cumulative release of aspirin over time for microspheres to which magnetic fields of frequencies between 0 and 20 Hz were applied. The field strength was fixed at 300 G. A higher frequency increased the aspirin release rate/efficiency as the frequency was varied from 0 Hz to 20 Hz.

It can be seen from the insets in FIGS. 3A and 3B that over a period of 6 hours, the rate of release of the aspirin could be enhanced by up to 9% by increasing the field strength from 0 to 300 G. Meanwhile, over 6 hours the amount of released aspirin could be enhanced by up to 26% by varying frequency. Tables 1 and 2 list the amount of aspirin released under different magnetic field strengths and frequencies.

TABLE 1

The amount of aspirin released from the microspheres under different magnetic field when frequency is 5 Hz.

| Time (h) | 0 G | 50 G | 100 G | 150 G | 200 G | 250 G | 300 G |
|---|---|---|---|---|---|---|---|
| 1 | 2.51 | 2.56 | 2.60 | 2.62 | 2.64 | 2.74 | 2.84 |
| 2 | 3.47 | 3.56 | 3.65 | 3.69 | 3.73 | 3.89 | 4.06 |
| 3 | 4.18 | 4.27 | 4.37 | 4.44 | 4.50 | 4.64 | 4.78 |

TABLE 1-continued

The amount of aspirin released from the microspheres under different magnetic field when frequency is 5 Hz.

| Time (h) | 0 G | 50 G | 100 G | 150 G | 200 G | 250 G | 300 G |
|---|---|---|---|---|---|---|---|
| 4 | 4.64 | 4.71 | 4.79 | 4.88 | 4.96 | 5.08 | 5.20 |
| 5 | 5.05 | 5.12 | 5.18 | 5.27 | 5.36 | 5.53 | 5.70 |

TABLE 2

The amount of aspirin released from the microspheres under different frequency when magnetic field is 300 G.

| Time (h) | 0 Hz | 5 Hz | 10 Hz | 15 Hz | 20 Hz |
|---|---|---|---|---|---|
| 1 | 2.52 | 2.66 | 2.81 | 2.94 | 3.07 |
| 2 | 3.47 | 3.76 | 4.03 | 4.25 | 4.46 |
| 3 | 4.18 | 4.54 | 4.91 | 5.23 | 5.57 |
| 4 | 4.65 | 5.20 | 5.50 | 5.92 | 6.37 |
| 5 | 5.05 | 5.70 | 6.00 | 6.51 | 7.06 |
| 6 | 5.38 | 5.98 | 6.45 | 6.98 | 7.56 |

In both Tables 1 and 2 the amount of aspirin released is in units of mg. So, for example, in Table 1 at 0 G of magnetic field 2.51 mg of aspirin where released after 1 hour.

Figure 3C:
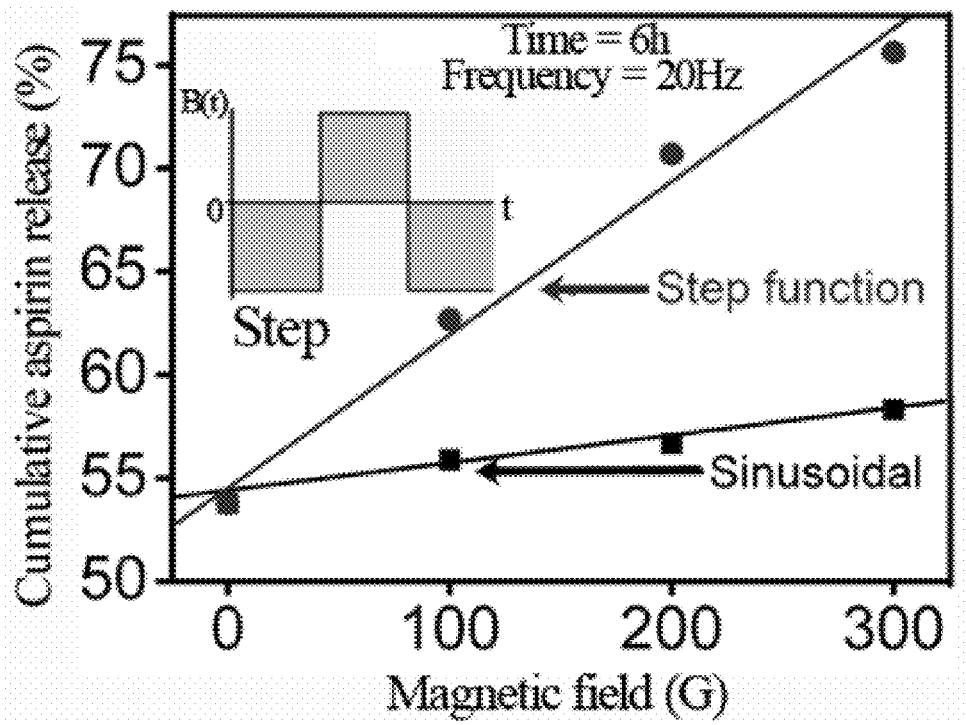
FIG. 3C shows drug release over time for a step waveform magnetic field.

Further experimentation showed that the time variation profile of the magnetic field also had an effect on the aspirin release rate. Both a step function magnetic field and a sinusoidal magnetic field were tested. FIG. 3c shows the variation in cumulative aspirin release for step function and sinusoidal magnetic fields of different strengths, with the frequency fixed at 20 Hz. It can be seen that as the field strength was raised at a fixed frequency (20 Hz), both the step function and sinusoidal time profiles resulted in a linear enhancement of the cumulative aspirin release. However, is the step function time profile shows a steeper slope than the sinusoidal one.

Figure 3D:
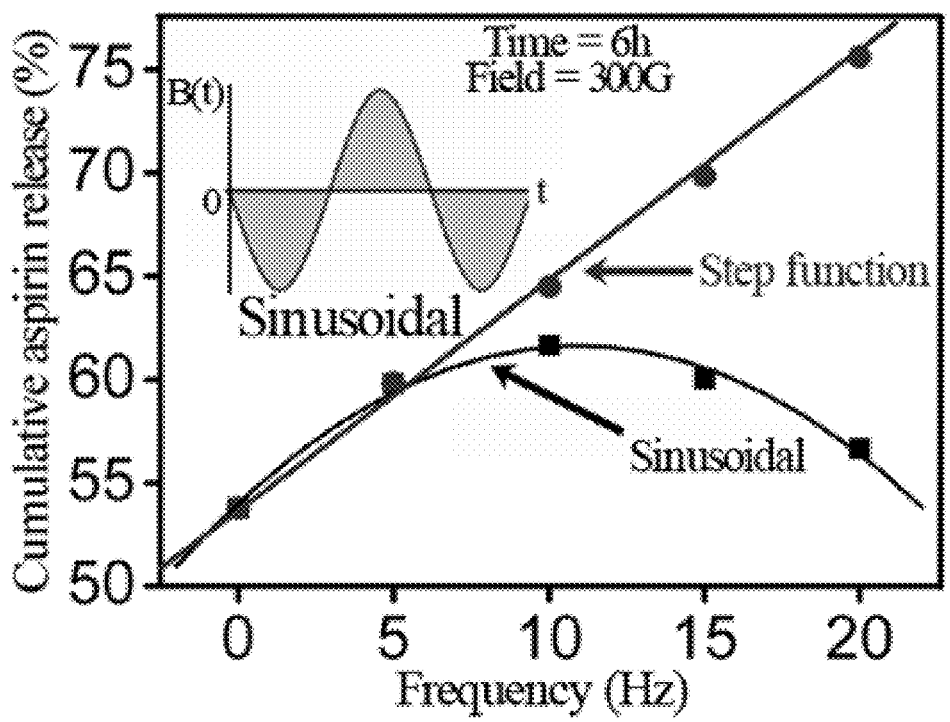
FIG. 3D shows drug release over time for a sinusoidal magnetic field.

FIG. 3D shows the variation in cumulative aspirin release for step function and sinusoidal magnetic fields of different frequencies, with the field strength fixed at 300 G. The two different time profiles yield almost the same aspirin release percentages for frequencies up to 5 Hz, but beyond that the step function time profile has a clear advantage in enhancing the aspirin release rate. Indeed for frequencies above about 10 Hz the rate of release for the sinusoidal time profile started to decline.

In general terms, the aspirin release rate is sensitive to sudden changes in the magnitude of the applied field. Thus the step function field leads to a larger rate of release than the sinusoidal field. It is believed that a saw wave function would be between these two extremes, having a greater rate of release than the sinusoidal function but less than the step function While reference has been made above to aspirin as the drug it is to be understood that any drug in liquid form could be substituted for the aspirin.

Figure 4:
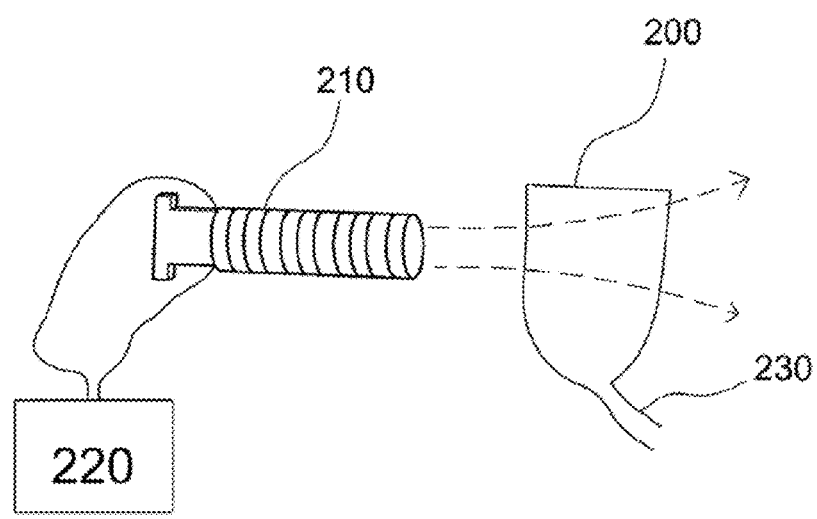
FIG. 4 shows an apparatus for dispensing a drug from microspheres.

FIG. 4 shows an apparatus for dispensing a liquid, e.g. a drug in liquid form, from the core of a microsphere. The apparatus comprises an electromagnet 210 for generating a varying magnetic field. The electromagnet 210 is powered by an AC current. Controller 220 controls the frequency, strength and time profile (e.g. step function, sinusoidal etc) of the magnetic field. The apparatus further comprises a container 200 containing a plurality of microspheres. The microspheres have a drug in liquid form in the core and a shell comprising magnetic particles in an organic matrix. The microspheres are elastically deformable in response to application of a magnetic field from the electromagnet 210. The container has an outlet 230 for to dispensing the drug released from the microspheres. The rate of release of the drug may be controlled by controlling the magnetic field as discussed above.

In other cases, the microspheres may be ingested by the patient and the patent may carry a device for generating an appropriate magnetic field (e.g. an electromagnet is which may be put in a pocket or worn on a strap.

Methods and apparatus for manufacturing the microspheres will now be described.

A preferred method of forming the microspheres is to use a microfluidic flow device. FIG. 5A shows a schematic diagram of an microfluidic flow (MFF) device, also known as a microfluidic chip. The device has first 10, second 20, third 30, fourth 40 and fifth 50 channels, each with an inlet tube for injecting fluid into the channel. The first 10, second 20 and third 30 channels join at a first junction 15 and combine to form a single sixth channel 60 (the 'main channel'). The fourth 40 and fifth 50 channels join with this sixth channel 60 at a second junction 25 downstream of the first junction 15. The second channel 20 is in the middle between the first and third channels. A seventh channel 70 joins the main channel 60 from the side and may be used to inject a de-wetting solution. Finally the MFF device has an outlet 80 at the end of the sixth channel 60. The first to fifth channels are preferably 200 μm in both depth and width. The main channel 60 is preferably 900 μm in width and in depth. However, the channels narrow towards the junctions in order to focus the flow of the fluids.

The MFF chip can be fabricated by first fixing a plexiglass channel mold on a plexiglass substrate. The mold is generated by laser cutting the substrate (e.g. laser cutting machine MT-MCSERIES). Polydimethylsiloxane (PDMS) gel is poured on the mold and placed in vacuum for 20 min to ensure layer uniformity. After curing, the PDMS layer with embedded channels was peeled off. This PDMS layer is then bonded to another half-cured PDMS layer to form sealed channels. Alternatively the MFF may be fabricated using soft-lithography.

The MFF device is used to make microspheres with a liquid core and a shell comprising magnetic particles. A first fluid which is a drug in liquid form (e.g. an aqueous solution of aspirin or amoxicillin) is injected into the second channel 20. Meanwhile, a second fluid which contains magnetic particles, is injected into the first and third channels. The first junction 15 has the effect of focusing the flow so that the liquid drug from the second channel is enveloped by a shell of the magnetic particle containing fluid from the first and third channels. At the second junction 25, the fluid is from the second channel is sheared to form droplets which are carried along down the main channel 60 by the carrier fluid from the fourth and fifth channels. This process is shown in FIGS. 5B to 5E.

A side channel 70 injects a de-wetting solution and cross-linking reagent to the main channel, which causes the shell of the droplets to solidify. Thus microspheres with a solid shell and liquid core are formed. The microspheres are carried along by the carrier fluid and deposited from the outlet 80.

An example of how the microspheres are formed and the chemical processes involved is described in more detail below.

Magnetite nanoparticles for the second fluid were prepared by a co-precipitation method. An aqueous solution containing 2 M hydrochloric acid and ferrous chloride was first mixed with 1 M ferrite chloride. 0.7 M ammonia solution was then added. The mixture was stirred for 30 mins and centrifuged at a speed of 10000 rpm; the supernatant solution was removed by decantation. The precipitates were rinsed with deionized water until pH=7 and then freeze-dried. The magnetic nanoparticles were dispersed by ultrasonic treatment for 3 hours in aqueous solution (100 ml) comprising low molecular weight chitosan (1.5 g) and 2 w/v % acetic acid. The suspension was subsequently centrifuged and freeze-dried to obtain the modified nanoparticles.

To prepare drug loaded microspheres, we used 1 w/v % aqueous solution of aspirin or amoxicillin as model drugs which were infused through the second channel 20. The model drugs injected was enveloped by streams composed of 2.5 g modified magnetite particles in 150 ml aqueous solution of 2 w/v % acetic acid and 1.5 w/v % of high molecular weight chitosan from the first and third channels 10, 30. The chemical hexadecan, with 0.5 w/v % span-80 was used as the carrying fluid and injected through the outermost channels (fourth channel 40 and fifth channel 50). With proper control of the relative flow rates of the streams in different channels, the drug solution in the second channel becomes unstable and breaks into uniform droplets. A core-shell double emulsion comprising an inner core of drug in liquid form (e.g. aspirin solution) and an outer shell of organic material and magnetic particles (e.g. is high molecular weight chitosan, embedded with magnetic nanoparticles) was thus formed. We employed a "dewetting" effect and cross-linking reaction to solidify the shell of the microsphere.

Figure 6A:
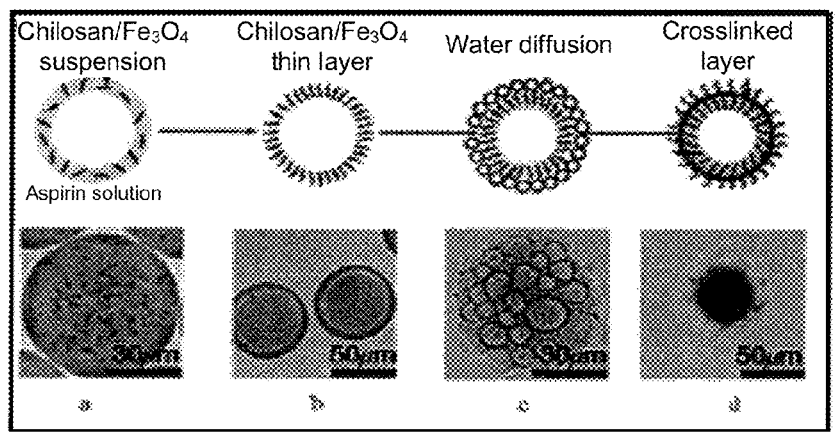
FIG. 6A is a diagram showing steps in solidifying the shell of the microsphere.
Figure 6B:
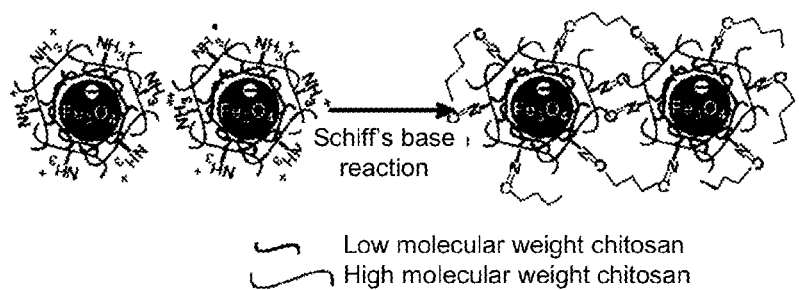
FIG. 6B is a diagram showing a Schiffs base reaction between glutaraldehyde and chitosan.

The seventh channel 70 was used to inject a dewetting solvent, n-butanol, and a cross-linking reagent, glutaraldehyde (comprising 10 w/v % glutaraldehyde in butanol). The solubility of n-butanol in water is 9.1 ml/100 ml at room temperature. FIG. 6A is a diagram showing steps in solidifying the shell of the microsphere. When the core-shell droplets (shown in FIG. 6 at (a)) flowed through the mixture of glutaraldehyde and butanol, water in the droplets was gradually drawn out by butanol, resulting in a thin outer layer (see FIG. 6 at (b) and (c)). We also tried ethanol, 1-propanol (both are fully miscible in water) and 1-pentanol (3.3 ml/100 ml water) as alternative "dewetting" reagents. The time required to fully dehydrate droplets varied. For ethanol and 1-propanol, the dehydrating time was less than 5 s. For n-butanol and 1-pentanol, the times were 20 s and 60 s respectively. In this experiment, the calculated residence time of droplets flowing in channel was 5-10 s, so we used n-butanol to partially absorb the water. FIG. 6B is a diagram showing a Schiffs base reaction between glutaraldehyde and chitosan. The resulting particles were then baked at 60° C. for 2 hr to facilitate Schiffs base reaction between glutaraldehyde and chitosan. By this reaction, a cross-linked layer was eventually formed (see FIG. 6 at (d) and FIGS. 6B and 6C).

Figure 6C:
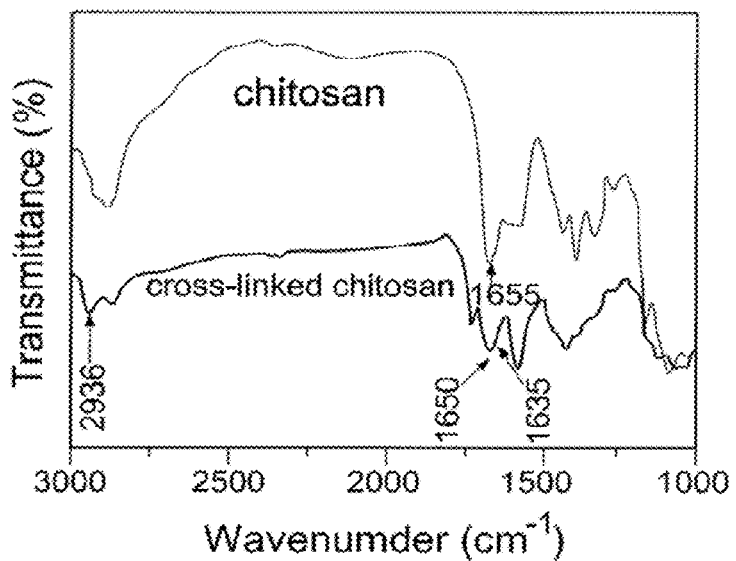
FIG. 6C is a FITR spectrogram showing the presence of chitosan and cross-linked chitosan in the microsphere.

We used Fourier transform infrared spectroscopy (FTIR) to confirm the primary amide bands of chitosan at 1655 cm$^{-1}$ split into peaks at 1635 cm$^{-1}$ and 1650 cm$^{-1}$ which are assigned to the C.dbd.N imines absorption. FIG. 6C is a FITR spectrogram showing the presence of chitosan and cross-linked chitosan in the microsphere. The increased intensity of C—H stretching vibration frequency at 2936 cm$^{-1}$ can also reflect the contribution of the glutaraldehyde molecules in the cross-linking chain. However, if the residence time is longer than dehydrating time, over-permeation of water can occur and lead to the complete shrinkage of the core-shell microspheres. To prevent over-dehydration of the droplets, a quenching process was preferably used to absorb the de-wetting agent. For example, where the de-wetting agent was butanol it could be absorbed by adding a solution of oleic acid in hexane (30 v/v %). We used three syringe pumps to control flow rates of the different liquids. The droplet sizes were adjustable in the range between 40 μm to 200 μm by varying the relative flow rates.

Magnetic Microspheres as Elastomers

Another embodiment of the disclosed technology will now be described. In this embodiment the microspheres do not have a liquid drug in the core. However, the microspheres are deformable by a magnetic field and have a stiffness which may be varied by application of a magnetic field. They may be used as magnetic elastomers in braking, shock absorption, as actuators or in other applications.

Figure 7A:
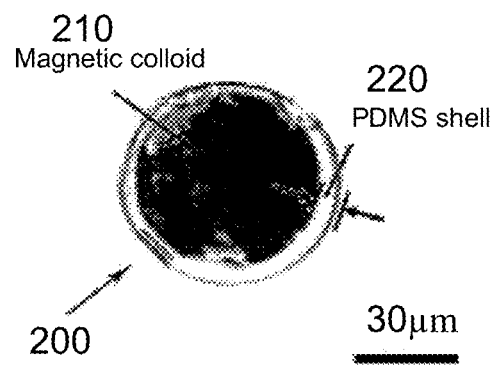
FIG. 7A is a SEM cross section of core shell structure.

FIG. 7A is a cross sectional SEM (scanning electron microscope) image of a core-shell microsphere 200. The core 210 of the microsphere is a magnetic colloid. The shell 220 of the microsphere is elastically deformable and comprises PDMS. In other embodiments the shell may be a different elastically deformable material. The modulus of elasticity of the shell should be at least 120 kPa (1.2.times.10$^5$ N/m$^2$), more preferably at least 200 kPa. In some arrangements the modulus of elasticity may be in the range 200-1000 kPa, or 350 to 800 kPa.

Figure 7B:
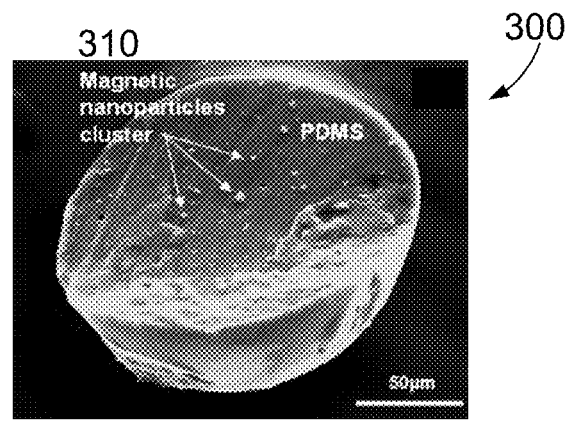
FIG. 7B is a SEM cross section of a solid structure.

FIG. 7B is a cross sectional (scanning electron microscope) image of a one phase microsphere 300. The microsphere 300 comprises magnetic particles 310 in an organic material matrix 320. The magnetic particles are randomly dispersed in the microsphere. The organic material matrix is elastically deformable, it may for example comprise PDMS or a rubber material. The organic material matrix should have a modulus of elasticity of at least 120 kPa (1.2.times.10$^5$ N/m$^2$), more preferably at least 200 kPa. In some arrangements the modulus of elasticity may be in the range 200-1000 kPa, or 350 to 800 kPa.

Figure 8:
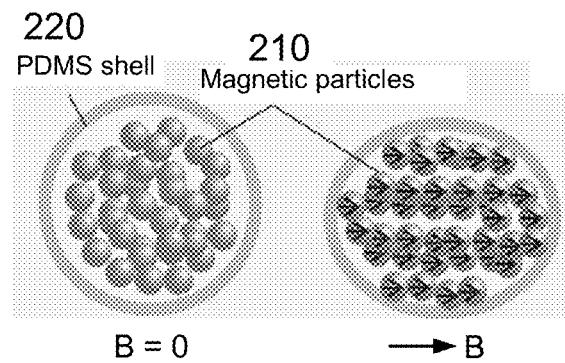
FIG. 8 shows the deformation of a core shell microsphere under application of a magnetic field.

Both the core-shell microsphere and the one phase microsphere can be deformed by application of a magnetic field. The core-shell arrangement of FIG. 7(a) is less deformable (e.g. less highly compressible) than the one phase arrangement of FIG. 7(b). FIG. 8 shows how the core shell microsphere is deformed by application of a magnetic field B. As can be seen, the magnetic particles in the core align with each other and stretch out along the field lines causing the shell to deform (stretch). The deformation is discussed in more detail below. However, first the method of forming the microspheres will be described.

Figure 9A:
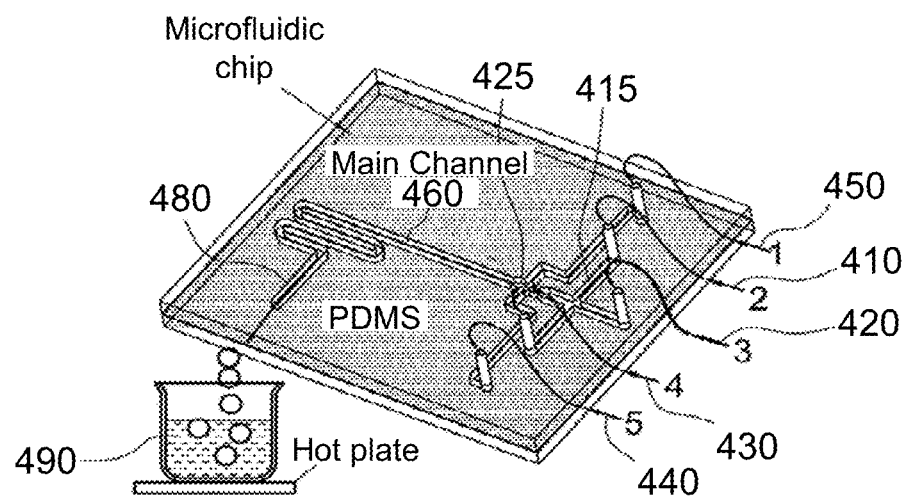
FIG. 9A shows a microfluidic chip for forming the microspheres.
Figure 9B:
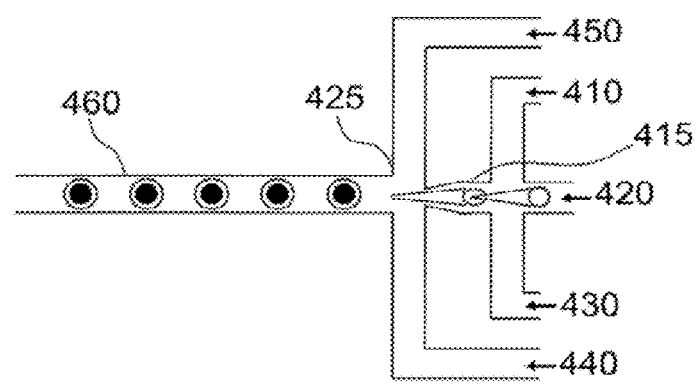
FIG. 9B is a schematic diagram of some channels of the microfluidic chip of FIG. 9A.

The microspheres are preferably fabricated by a microfluidic flow device (MFFD), e.g. as shown in FIGS. 9A and 9B. The device has first 410, second 420, third 430, fourth 440 channels and fifth 450 channels, each with an inlet tube for injecting fluid into the channel. The first 410, second 420 and third 430 channels join at a first junction 415 and combine to form a single sixth channel 460 (the 'main channel'). The fourth 440 and fifth 450 channels join with this sixth channel 460 at a second junction 425 downstream of the first junction 415. The second channel 420 is in the middle between the first and third channels. The MFF device has an outlet 480 at the end of the sixth channel 460. The first to fifth channels are preferably 200 μm in both depth and width. The main channel 460 is preferably 900 μm in width and in depth. However, the channels narrow towards the junctions in order to focus the flow of the fluids. Two glass capillaries (e.g. 150 mm in inner diameter) may be inserted at the two junctions for this purpose. In that case, the gaps between the glass capillaries and the inner channel walls may be filled with PDMS gel to prevent stream branching.

The MFF chip can be fabricated by first fixing a plexiglass channel mold on a plexiglass substrate. The mold is generated by laser cutting the substrate (e.g. laser cutting machine MT-MCSERIES). Polydimethylsiloxane (PDMS) gel is poured on the mold and placed in vacuum for 20 min to ensure layer uniformity. After curing, the PDMS layer with embedded channels was peeled off. This PDMS layer is then bonded to another half-cured PDMS layer to form sealed channels. Alternatively the MFF may be fabricated using soft-lithography.

A method of making the core-shell microspheres of FIG. 7A will now be described. A first fluid which comprises magnetic particles (e.g a magnetic colloid) is injected into the second channel 420. Meanwhile, a second fluid which is a PDMS gel is injected into the first and third channels. By adjusting the flow rates of the five channels appropriately, the first junction 415 has the effect of focusing the flow so that the magnetic colloid from the second channel is enveloped by a shell of the PDMS fluid from the first and third channels. At the second junction 425, the fluid from the to second channel breaks up to form droplets which are carried along down the main channel 460 by the carrier fluid from the fourth and fifth channels. The droplets quickly form a spherical shape due to interfacial tension. Thus microspheres with a solid shell and liquid core are formed. The carrier fluid from the fourth and fifth helps to prevent the PDMS gel from touching the main channel walls.

The microspheres are carried along by the carrier fluid and deposited from the outlet 80. The core-shell microspheres were solidified by heating in a beaker 490 containing sunflower oil at 120° C. Under this relatively high temperature, the PDMS gel was rapidly cured. Solid and monodispersed microspheres were obtained by continuously stirring the oil during the solidification process.

In one example, the first fluid was a magnetic colloid having a viscosity of 140 mPa and consisting of magnetic nanoparticles $Fe_3O_4$_dispersed in sunflower oil at a particle concentration of 30% by weight of $Fe_3O_4$. The second fluid was PDMS gel diluted by silicone oils at a concentration of 77% by weight PDMS, having a viscosity of 600 mPa. The carrier fluid was sunflower oil, in particular Soon Hup Co. Ltd., sunflower oil with a viscosity of 60 mPa, which was found particularly suitable due to its nonwetting characteristics.

The microfluidic device of FIG. 9A was also used to fabricate solid one phase microspheres consisting of magnetic particles embedded in PDMS matrix. This was done by replacing the PDMS gel in the first and third channels with PDMS-based mixtures having a viscosity of 830 mPa and consisting of PDMS gel, silicone oil, and magnetic particles at a particle concentration of 20%_by weight of magnetic particles. The central second channel was not used.

Figure 10:
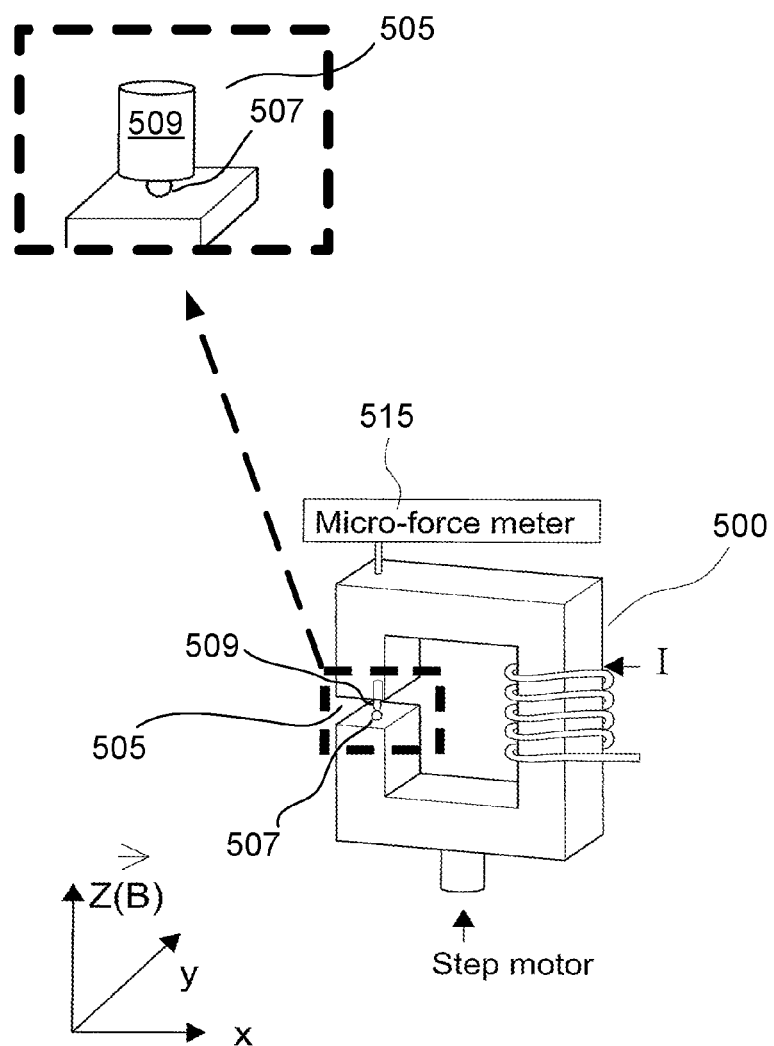
FIG. 10 is a schematic diagram of an apparatus for measuring the deformation and deformation force when a magnetic field is applied to the microsphere.

To gain a more quantitative understanding of the mechanical properties of both the core-shell microspheres and solid (one phase) microspheres, we studied their magnetostrictive effect using the setup illustrated in FIG. 10. The set comprised a horseshoe electromagnet 500 with a 5 mm gap 505 between its ends. The electromagnet 500 was driven by a direct current amplifier. A microsphere 507 was placed in the gap and the deformation process of the microsphere was monitored by a charge coupled device camera (not shown) and recorded with a video recorder (not shown). A plastic rod 509 of 1 mm in diameter and a microforce meter 515 were used to measure the force as the microsphere was is deformed by the magnetic field. The plastic rod 509 was positioned with a first end linked to a microforce meter 515 and the second end passing through a hole drilled on an opened arm. The second end of the plastic rod just touched the surface of the microsphere 507.

The plastic rod 509 was adjusted to ensure that it did not touch the wall of the drilled hole. The microforce meter was modified by a precision weighting balance _OHAUS, ANALYTICAL Plus with an accuracy of 0.01 mg. The exact position of the setup could me moved up and down by a step motor with a step size of 5 µm. The force acting on the microsphere was measured by the micro-force meter 515. The force was reset to zero when the second end of the plastic rod just contacted the microsphere in the absence of a magnetic field.

Figure 11A:
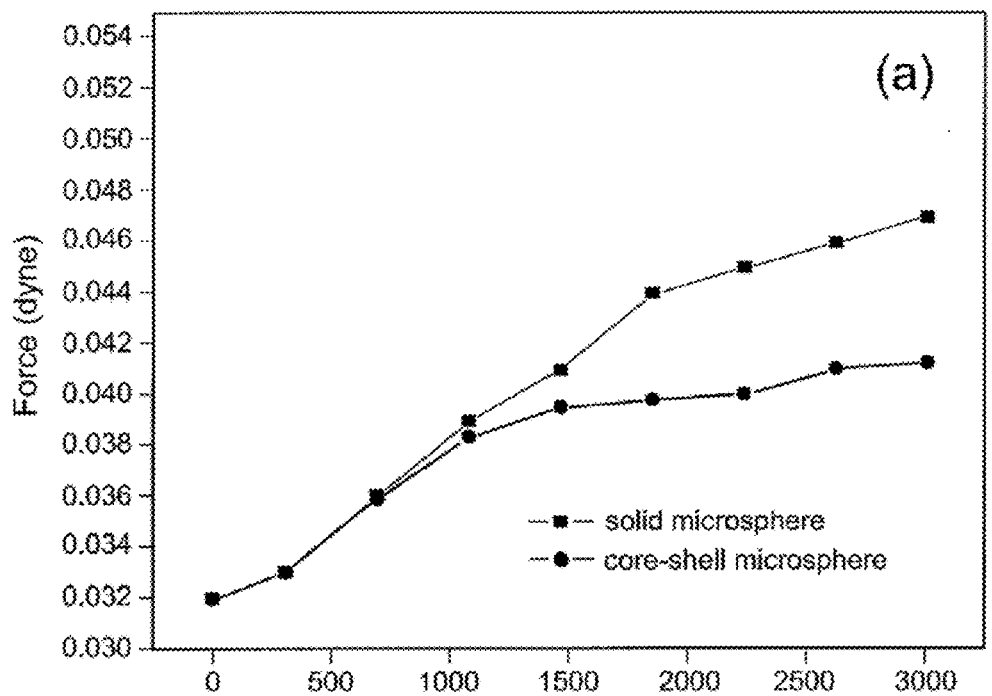
FIG. 11A is a graph showing the variation in deformation force with magnetic field for solid and core-shell microspheres.

FIG. 11A shows the measured force as a function of the applied magnetic field. The application of a magnetic field led to an elongation of the microsphere along the field direction. The resulting push against the rod caused a measurable deformation force represented by the y-axis of FIG. 11A. FIG. 11A shows the measured deformation force for both a core-shell microsphere and a solid (one phase) microsphere. The results for the core shell microsphere are shown as circles, while the results for the solid microsphere are shown as squares. For both types of microsphere, the deformation force increased monotonically as a function of applied magnetic field. The deformation force tended to saturation when the field strength was above 1500 G.

Figure 11B:
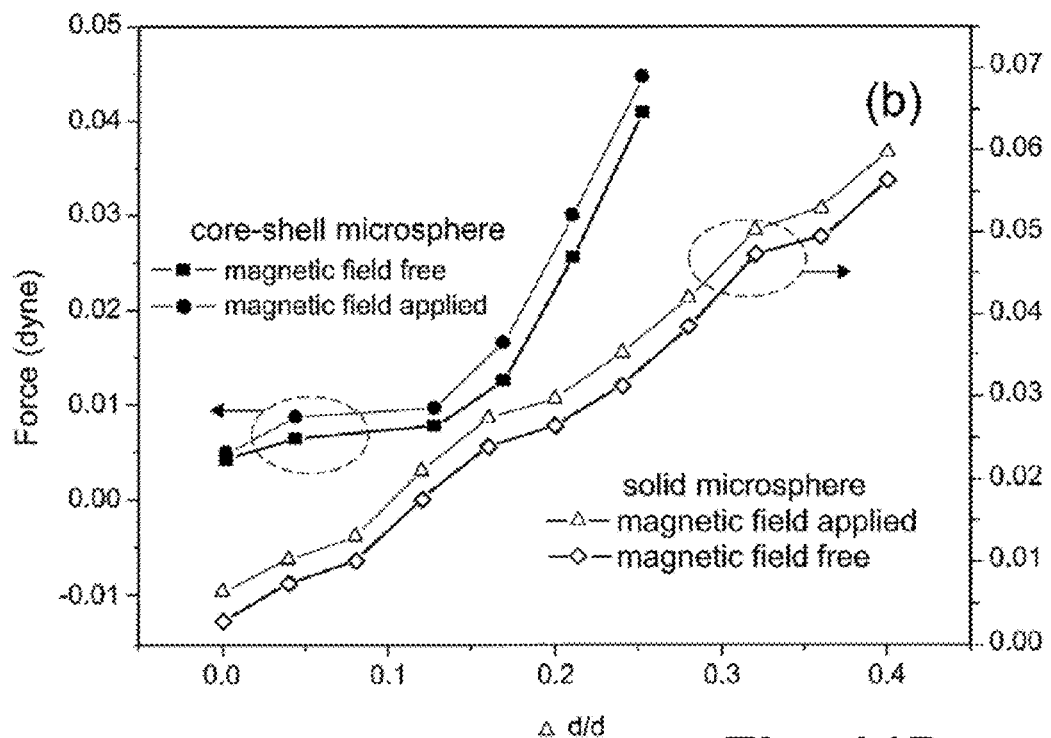
FIG. 11B is a graph showing the variation in deformation force for various degrees of mechanically applied deformation for both solid and core-shell microspheres in the presence of a magnetic field and in the absence of a magnetic field.

In FIG. 11B the measured deformation force is plotted as a function of $\Delta d/d$. Where d is the diameter of the microsphere and $\Delta d$ is the change of diameter. Deformation of the microsphere was caused by using the step motor to drive the stage upward in measured amounts. As the stage moved upward the plastic rod compressed the microsphere causing its horizontal diameter to expand. The reaction force felt by the rod was measured by a microforce meter. For a fixed $\Delta d/d$ the graph shows two values for the force; firstly the force when a constant magnetic field of 3000 G was applied and secondly the force when no magnetic field was applied. For both solid and core-shell microspheres, there was a clear increase in the measured force by approximately 5 mdyn at a fixed value of $\Delta d/d$. In other words presence of a magnetic field caused the microsphere to be harder and more resistant to deformation from an external force. In other words the application of an external magnetic field increased the deformation modulus of the microsphere. PDMS is magnetically inactive and therefore this increase in stiffness is thought to be due to a combination of interaction of the magnetic particles with the applied magnetic field and interaction between magnetic particles.

In summary, for both core-shell microspheres and solid microspheres, the deformation (stretch along the direction of the magnetic field) and the stiffness of the microsphere increases with the applied magnetic field. However, for the core-shell microsphere the stretching deformation tends to saturate earlier when the magnetic field reaches a certain critical value (about 1500 G in FIG. 11A). Further, as can be seen in FIG. 11B, the core-shell microsphere is less compressible than the solid microsphere.

Although the above description exemplifies a few embodiments of the disclosed technology, it should be understood that various omissions, substitutions, and changes in the form of the detail of the apparatus, system, and/or method as illustrated as well as the uses thereof, may be made by those skilled in the art, without departing from the spirit of the present invention. Consequently, the scope of the present invention should not be limited to the disclosed embodiments.

The invention claimed is:

1. A method of forming a microsphere comprising the steps of:
   providing a first fluid;
   providing a second fluid comprising magnetic particles and a material capable of forming an elastically deformable material; and
   mixing said first and second fluids such that the first fluid forms a core of the microsphere and remains in a fluid state in the microsphere and the second fluid forms an elastically deformable shell of the microsphere comprising at least one different material from the core of the microsphere providing a cross-linked structure, forming a solid skin for the microsphere, and comprising the magnetic particles, and the material capable of forming the elastically deformable material which exhibits an increase in permeability when distorted, wherein, in response to a magnetic field, the magnetic particles in the elastically deformable shell cause said elastically deformable shell to deform, resulting in increased permeability of the shell, thereby providing controlled release of a liquid comprising the first fluid from the core of the microsphere in accordance with a magnetic field property, the magnetic field property consisting of at least one of strength of the magnetic field, frequency of the magnetic field and the type of waveform of the magnetic field.

2. The method of claim 1 wherein the first fluid comprises a drug.

3. The method of claim 1 wherein said first and second fluids are mixed using a fluid flow device comprising a plurality of channels.

4. The method of claim 3 wherein there are at least first, second and third channels, said second channel being provided between said first and third channels, said first and third channels joining with said second channel at a first junction; and wherein the first fluid is injected into the second channel and the second fluid is injected into the first and third channels.

5. The method of claim 4 wherein said first, second and third channels are provided between fourth and fifth channels, said fourth and fifth channels joining said second channel at a second junction which is downstream of said first junction; and wherein the method further comprises the step of injecting carrier fluid into said fourth and fifth channels.

6. The method of claim 1 further comprising a process for solidifying the shell from a liquid to form a magnetically deformable elastomeric shell.

* * * * *